US012714611B2

(12) United States Patent
Mandotti

(10) Patent No.: US 12,714,611 B2
(45) Date of Patent: Aug. 25, 2026

(54) FORMING STATION FOR FORMING AN ABSORBENT CORE FOR DISPOSABLE HYGIENE PRODUCTS

(71) Applicant: TEKNOWEB CONVERTING SRL, Palazzo Pignano (IT)

(72) Inventor: Pierangelo Mandotti, Palazzo Pignano (IT)

(73) Assignee: TEKNOWEB CONVERTING SRL, Palazzo Pignano (IT)

(*) Notice: Subject to any disclaimer, the term of this patent is extended or adjusted under 35 U.S.C. 154(b) by 0 days.

(21) Appl. No.: 19/103,510

(22) PCT Filed: Jul. 19, 2023

(86) PCT No.: PCT/IT2023/050167

§ 371 (c)(1),
(2) Date: Feb. 12, 2025

(87) PCT Pub. No.: WO2024/033953

PCT Pub. Date: Feb. 15, 2024

(65) Prior Publication Data

US 2026/0053677 A1 Feb. 26, 2026

(30) Foreign Application Priority Data

Aug. 8, 2022 (IT) ........................ 102022000016908

(51) Int. Cl.
*A61F 13/00* (2024.01)
*A61F 13/15* (2006.01)

(52) U.S. Cl.
CPC .. *A61F 13/15642* (2013.01); *A61F 13/15764* (2013.01); *A61F 2013/15926* (2013.01)

(58) Field of Classification Search
CPC . B26D 1/141; B26D 1/16; B26D 1/58; B26D 2007/206; B26D 7/0625;

(Continued)

(56) References Cited

U.S. PATENT DOCUMENTS 4,640,810 A * 2/1987 Laursen ................. D04H 1/732 264/518
5,415,717 A * 5/1995 Perneborn ......... A61F 13/15642 118/301
2020/0330286 A1* 10/2020 Rosani ............. A61F 13/15764

FOREIGN PATENT DOCUMENTS

WO WO-2022034468 A1 * 2/2022 ....... A61F 13/15658

OTHER PUBLICATIONS

International Search Report and Written Opinion of the ISA for PCT/IT2023/050167, mailed Sep. 22, 2023, 9 pages.

* cited by examiner

*Primary Examiner* — Jacob A Smith
(74) *Attorney, Agent, or Firm* — NIXON & VANDERHYE

(57) ABSTRACT

The invention concerns the sector of production and packaging lines for disposable hygiene products, for example nappies and/or absorbent underpads for babies, adults and animals. In further detail, the invention concerns a forming station (1) for forming an absorbent core for disposable hygiene products of the type comprising at least one ply (2) scattered with cellulose. Said forming station (1) comprises:—a frame (3);—means for feeding cellulose flakes adapted to convey a flow of cellulose flakes towards said ply, and means for feeding a ply (2) in a feed direction (x);—a perforated belt (5) adapted to support said ply as it is fed forward;—a suction hood (6), positioned below said belt (5), adapted to suck said cellulose, causing it to lie flat on said ply (2);—a plurality of horizontal axis rotating brushes (7), arranged transversally to the feed direction (x) of said ply (2);—a screen (8) comprising a plurality of holes (8') arranged between said brushes (7) and said ply (2);—"come and go" alternating movement means for said screen (8) parallel to the feed direction (x) of said ply (2); wherein said (Continued)

brushes (7) are functionally in contact with said screen (8) and said cellulose flakes are adapted to pass through said holes (8') of said screen (8) facilitated by said suction hood (6) and by the combined movements of said brushes (7) and said screen (8).

18 Claims, 8 Drawing Sheets

(58) Field of Classification Search
CPC .............. B26D 7/20; B65H 2301/4474; B65H 2301/4476; B65H 2404/232; B65H 2404/2321
USPC ........ 156/265, 538, 269, 291, 510; 162/124, 162/125, 117, 127, 158
See application file for complete search history.

1
29
7
4
26
4
7
8
3
9
X
X
33
5
33
5
6
33

9
9a
9b
9c
9d
10
11
12
2
30
34
35
36
37
38

4
7
8
9
10
29
41
14
13'
13
13"
16
39'
39
39"
40
40'
40"
2
8'
27
8

6
17
18
19
20
21
22
22

22
21
22
18'
18
23
25
42

22
21
22
44
45
43
43
23
18
25
42

FORMING STATION FOR FORMING AN ABSORBENT CORE FOR DISPOSABLE HYGIENE PRODUCTS

CROSS-REFERENCE TO RELATED APPLICATIONS

This application is the U.S. national phase of International Application No. PCT/IT2023/050167 filed Jul. 19, 2023 which designated the U.S. and claims priority to IT 102022000016908 filed Aug. 8, 2022, the entire contents of each of which are hereby incorporated by reference.

TECHNICAL FIELD OF APPLICATION

The invention concerns the sector of production and packaging lines for disposable hygiene products, for example nappies and/or absorbent underpads for babies, adults and animals.

In further detail, the invention concerns a forming station for forming an absorbent core for disposable hygiene products of the type comprising at least one ply scattered with cellulose.

PRIOR ART

The forming stations for forming absorbent cores receive the cellulose flakes produced by a grinding mill and, with the help of a suction hood, distribute them on a ply, also made of cellulose, which is unwound and fed in a feed direction.

A forming station of known type comprises:

a frame;

means for feeding cellulose flakes comprising at least one duct adapted to convey a flow of cellulose flakes towards said ply;

a perforated belt adapted to support said ply as it is fed forward;

a suction hood, positioned below said belt, adapted to suck said cellulose causing it to lie flat on said ply;

a rotating levelling brush, positioned downstream of said duct through which the cellulose is fed and above said ply so as to lightly touch it, adapted to level the layer of cellulose flakes just deposited on said ply.

Based on different possible applications, said suction hood can be of the rotary or flat belt type, consequently modifying the geometry and distribution of the various mechanical components, while maintaining the same functions.

Said forming stations have some limits and drawbacks, particularly evident in production lines that are becoming faster and faster, and for the formation of particularly thin absorbent cores.

A first drawback derives from the fact that the cellulose flakes taken from the grinding mill, due to the turbulent motion created by suction of the hood, tend to become electrostatically charged and clump together when deposited on the ply.

Consequently, the cellulose deposits on the ply in a non-uniform manner: empty spaces alternate with clumps of cellulose which it is difficult for the levelling brush located downstream to distribute.

In any case, a huge expenditure of energy is required of said levelling brush, with consequent increase in consumption.

Said drawbacks are more evident for thinner and therefore very light absorbent cores (weighing less than 15 g/m2).

PRESENTATION OF THE INVENTION

The invention aims to overcome these limits, providing a forming station for forming an absorbent core for disposable hygiene products that uniformly distributes the cellulose flakes, also with minimum thicknesses and gram weights, and is efficient, accurate, and speeds up production.

A further object of the present invention is to obtain an absorbent core which:

is thin, to facilitate subsequent packaging of the hygiene product that contains it, to reduce the volume of the finished packages, optimise use of the warehouse space and reduce transport costs;

is provided with a uniform cellulose layer so as to be uniformly absorbent;

has high quality and finish, to reduce user discomfort.

Said objects are achieved by a forming station for forming an absorbent core for disposable hygiene products of the type comprising at least one ply scattered with cellulose, where said forming station comprises:

a frame;

means for feeding cellulose flakes comprising at least one duct adapted to convey a flow of cellulose flakes towards said ply;

means for feeding a ply in a feed direction;

a perforated belt adapted to support said ply as it is fed forward;

a suction hood, located below said belt, adapted to suck said cellulose causing it to lie flat on said ply, characterised in that it comprises:

a plurality of horizontal axis rotating brushes, arranged transversally to the feed direction of said ply;

a screen comprising a plurality of holes arranged between said brushes and said ply;

"come and go" alternating movement means for said screen parallel to the feed direction of said ply;

where said brushes are functionally in contact with said screen and said cellulose flakes are adapted to pass through said holes of said screen facilitated by said suction hood and by the combined movements of said brushes and said screen.

According to a first aspect of the invention, said forming station comprises a collection unit of said cellulose, arranged between said screen and said perforated belt, and closed peripherally so that it can be placed under a vacuum by said suction hood.

In particular, said collection unit comprises a first pair of lateral walls parallel to the feed direction of said ply and a second pair of lateral walls orthogonal to said feed direction.

Advantageously, said forming station comprises adjustment means for adjusting the reciprocal position of the said lateral walls parallel to the feed direction of said ply, to vary the dimension of said collection unit according to the width of the ply.

According to further aspects of the invention, each lateral wall orthogonal to said feed direction comprises a roller adapted to rest on said ply to seal said collection unit, allowing said ply to be fed forward.

Advantageously, said collection unit comprises a sealing system with scraper blades positioned in contact with each roller and ensuring the airtightness of said collection unit.

According to a possible embodiment, said "come and go" alternating movement means of said screen comprise at least a connecting rod and crank mechanism.

In particular, said crank is made of a wheel comprising, along a radius thereof, selective fixing means for said connecting rod, in order to adjust the range of the "come and go" alternating movement of said screen.

Advantageously, said frame comprises tracks and said screen comprises wheels adapted to cooperate with said tracks.

In a preferred embodiment, said suction hood comprises an extractor, a horizontal conveyor and a vertical conveyor joined to one another by means of a flange.

According to a further aspect, said horizontal conveyor comprises a suction inlet on which said perforated belt runs, said ply resting on the latter, and said suction inlet comprises blade shuttering means for adjusting the opening thereof.

In a possible variation of the invention, said horizontal conveyor and vertical conveyor each comprise a plurality of inner walls that divide them into horizontal chambers and vertical chambers respectively.

Even more preferably said horizontal conveyor and said vertical conveyor comprise shutters adapted to regulate the suction flow of said chambers, and control means for said shutters that can be operated externally.

In a possible variation of the invention, said cellulose flake feeding means comprise two ducts, arranged in sequence in the feed direction of said ply; a feed duct for feeding super-absorbent material is interposed between said ducts.

In particular, said screen comprises a central opening directly connected to said feed duct for feeding super-absorbent material, thus favouring the direct deposition thereof between a first and a second layer of cellulose flakes.

The invention has numerous advantages.

The rotation movement of the brushes combined with the "come and go" alternating movement of the screen favours uniform distribution of the cellulose flakes on the ply, facilitated by the suction of the suction hood.

The rotating brushes lightly touch the surface of the screen, accompanying the cellulose flakes towards the holes of the screen.

The "come and go" alternating movement of the screen guarantees uniform distribution of the cellulose, thus obtaining a substantially constant layer thereof on the ply.

The uniform thickness of the cellulose results in a layer without lumps or empty spaces, with the advantage of obtaining a final core with uniform absorbent capacity.

Advantageously, with a correct distribution of the cellulose, the required absorbent power being equal, it is possible to obtain thinner and lighter cores, with a weight in the order of 10-15 g/m2.

A possible change of screen, with appropriately-sized holes, allows different quantities of cellulose to be dosed, without having to intervene on other components of the forming station.

The levelling brush traditionally positioned downstream of the cellulose feed duct is no longer required.

The forming station can be easily adapted to the format of the ply.

The suction system can be easily shuttered to optimise the vacuum flow.

BRIEF DESCRIPTION OF THE DRAWINGS

The advantages of the invention will become clearer from the following description, which describes a preferred embodiment, by way of non-limiting example, and with the help of the figures in which.

DETAILED DISCLOSURE OF A PREFERRED EMBODIMENT OF THE INVENTION

With reference to the Figures, a forming station 1 for forming an absorbent core for disposable hygiene products such as, for example, nappies or absorbent underpads for children, adults or animals, is illustrated.

Said absorbent core is of the type comprising at least a ply 2 scattered with cellulose flakes. In possible variations, said absorbent core also comprises granules of super-absorbent material, retained between said cellulose.

Said ply 2, also made of cellulose, is normally supplied in reels and unwound upstream of the forming station 1.

Said cellulose flakes are produced by a grinding mill also located upstream of the forming station 1.

The forming station 1 illustrated is of the flat chamber type, but the same characteristics can apply also to drum forming stations, which represent a variation in which the perforated belt runs on a drum placed in a vacuum and the forming chamber is shaped to adapt to the drum.

Figure 1:
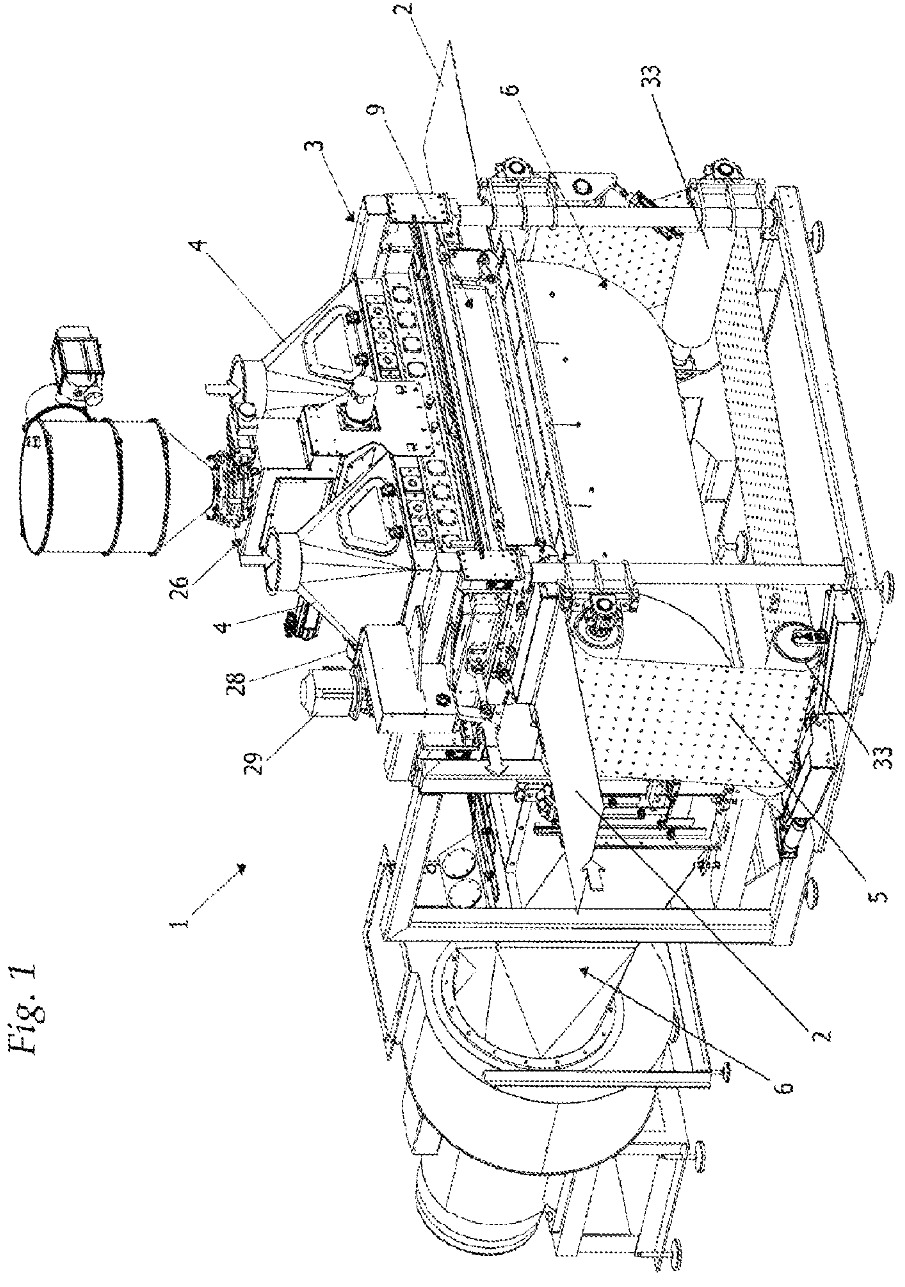
FIGS. 1 and 2 show, in axonometric view and in longitudinal section along a vertical plane respectively, a forming station for forming an absorbent core for disposable hygiene products according to the invention.
Figure 2:
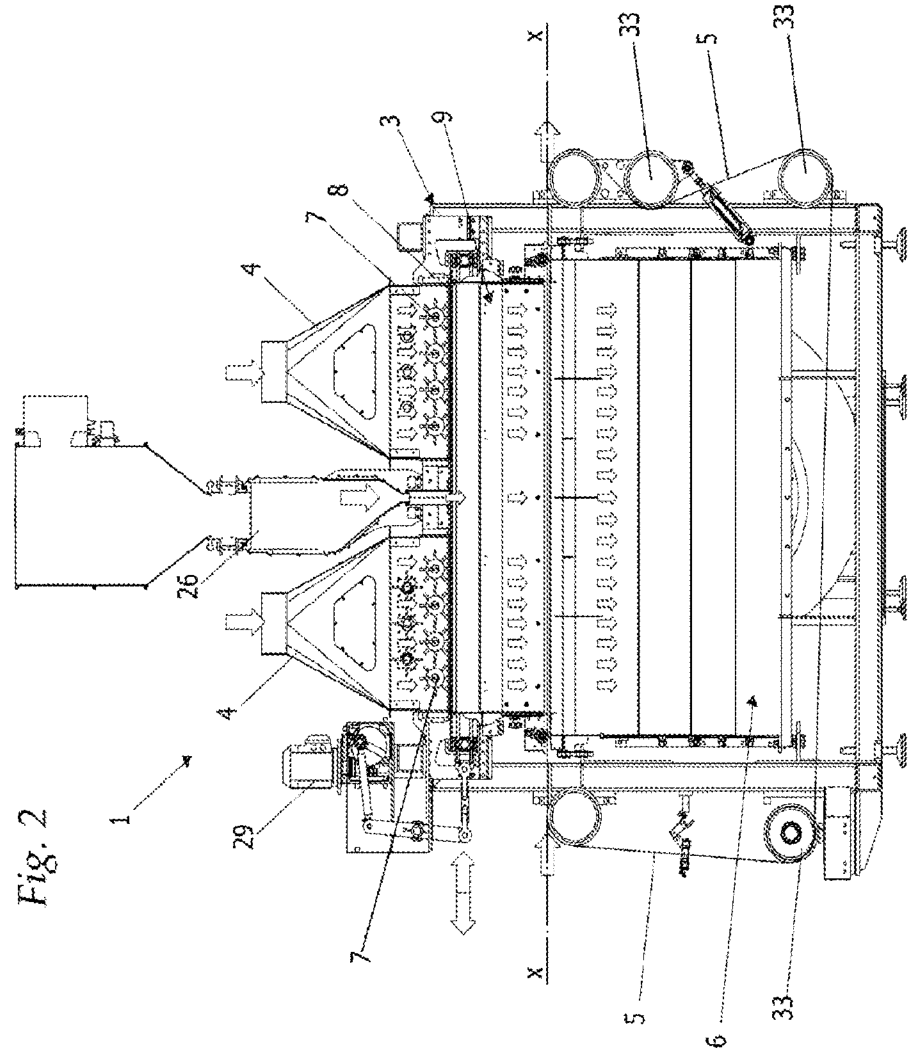

With reference to the assembly FIGS. 1-2, said forming station 1 comprises essentially:

- a frame 3;
- means for feeding cellulose flakes comprising at least one duct 4, or rather two ducts 4, adapted to convey a flow of cellulose flakes towards said ply 2;
- a perforated belt 5 adapted to support said ply 2 as it is fed forward in a direction x;
- a suction hood 6, positioned below said perforated belt 5, adapted to suck said cellulose, causing it to lie flat on said ply 2;
- a plurality of horizontal axis rotating brushes 7, arranged transversally to the feed direction x of said ply 2;
- first motor means 28 for said brushes 7;
- a screen 8 comprising a plurality of holes 8' arranged between said brushes 7 and said ply 2;
- "come and go" alternating movement means for said screen 8 parallel to the feed direction x of said ply 2;
- second motor means 29 for said screen 8;
- a collection unit 9 of said cellulose, arranged between said screen 8 and said perforated belt 5, and peripherally closed so that it can be placed under a vacuum by said suction hood 6.

Said brushes 7 are functionally in contact with said screen 8 so as to lightly touch it with their ends, and each of them is provided with their own motor means 28.

Figures 7, 8:
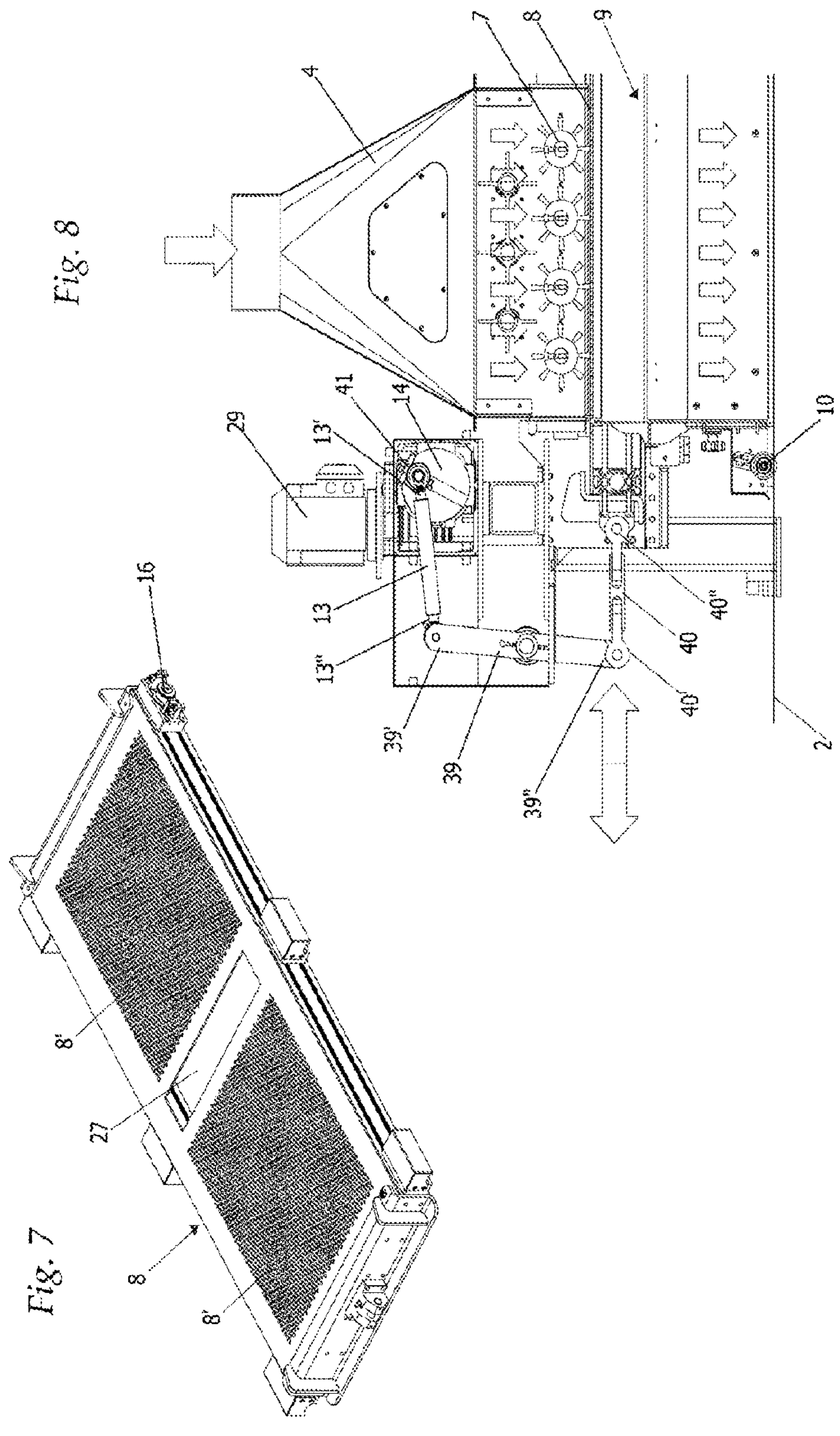
FIG. 7 shows, in axonometric view, a component of the forming station of FIG. 1.
FIG. 8 shows a detail of the section of FIG. 2.
Figure 9:
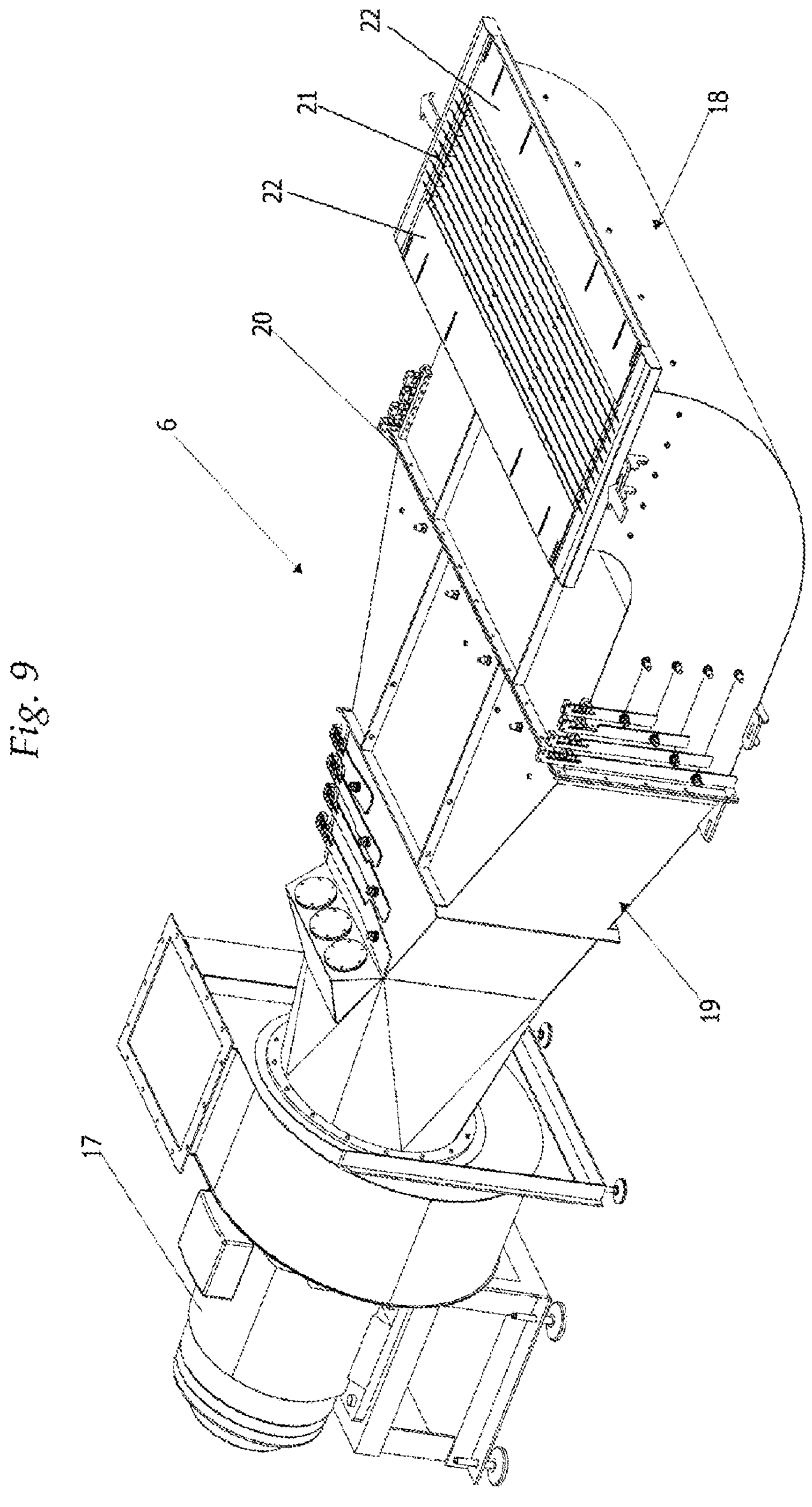
FIG. 9-13 show, in axonometric view, components of the forming station, according to a possible variation of the invention.
Figures 10, 11:
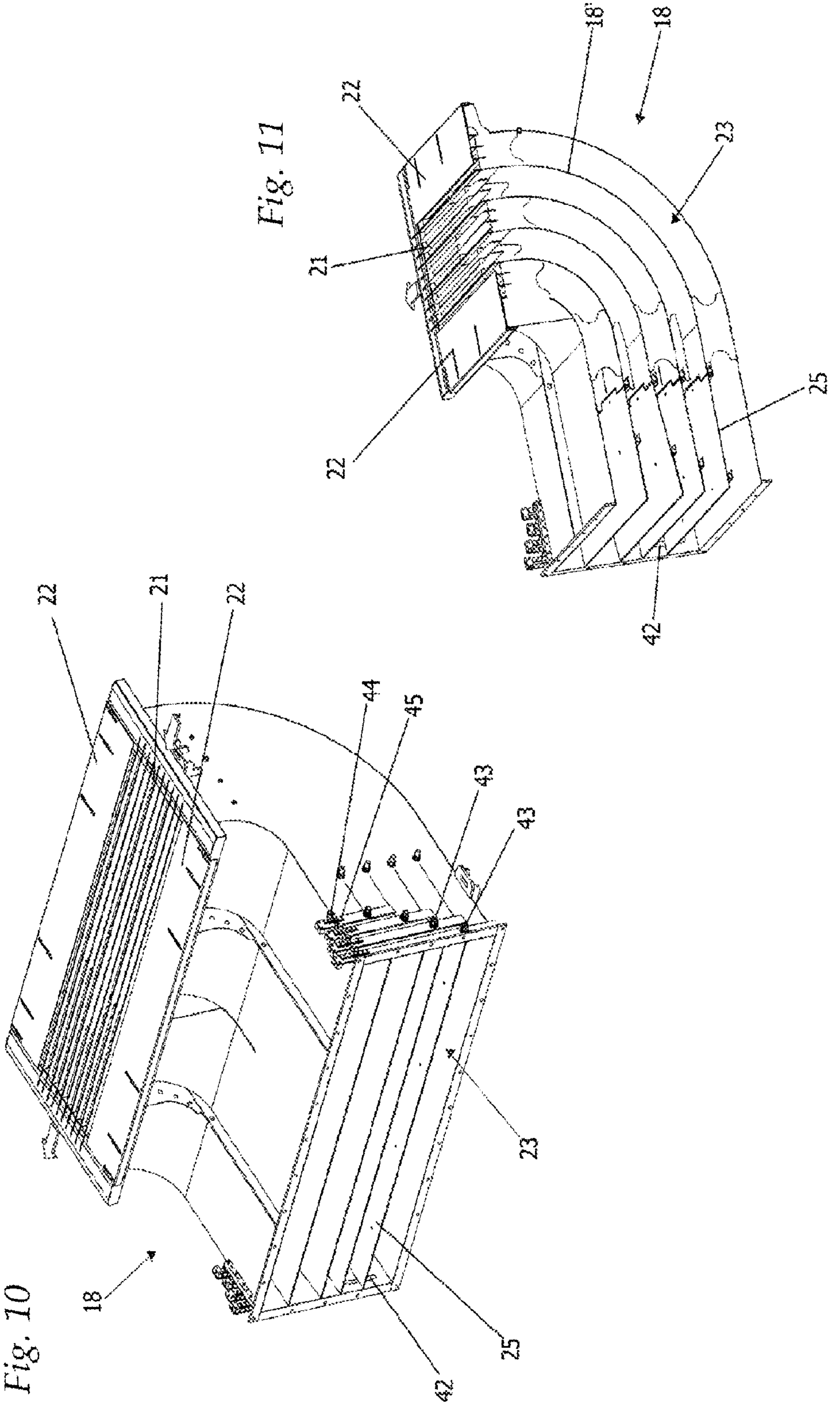
Figure 13:
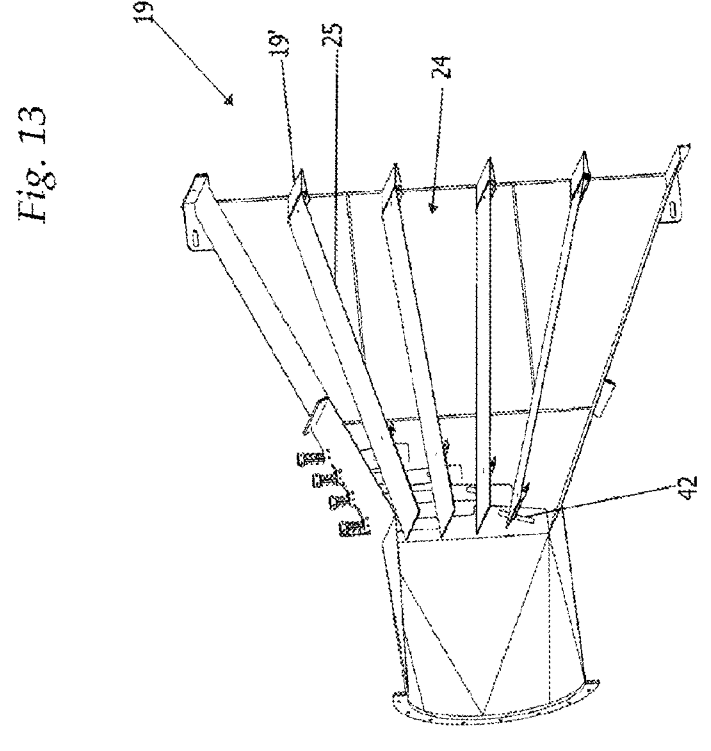
Figure 12:
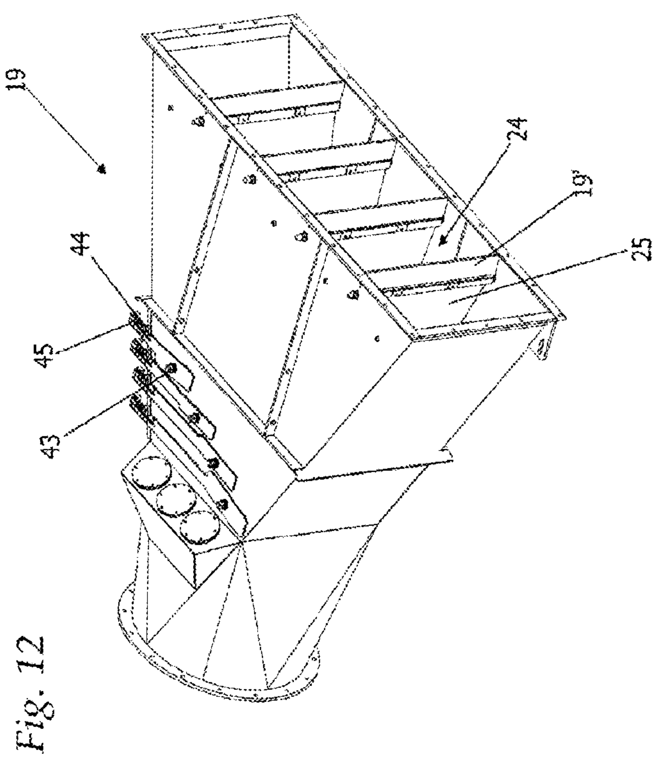

Substantially, said brushes 7 are adapted to lightly touch said screen 8 during their rotation movement, while the holes 8' of said screen 8, illustrated in the detail of FIG. 7, allow passage of the cellulose from the feed ducts 4 to the collection unit 9, until reaching the ply 2.

Said cellulose flakes are adapted to pass through said holes 8' of said screen 8 facilitated by said suction hood 6 and by the combination of the rotary movement of said brushes 7 and the "come and go" alternating movement of said screen 8.

Figure 3:
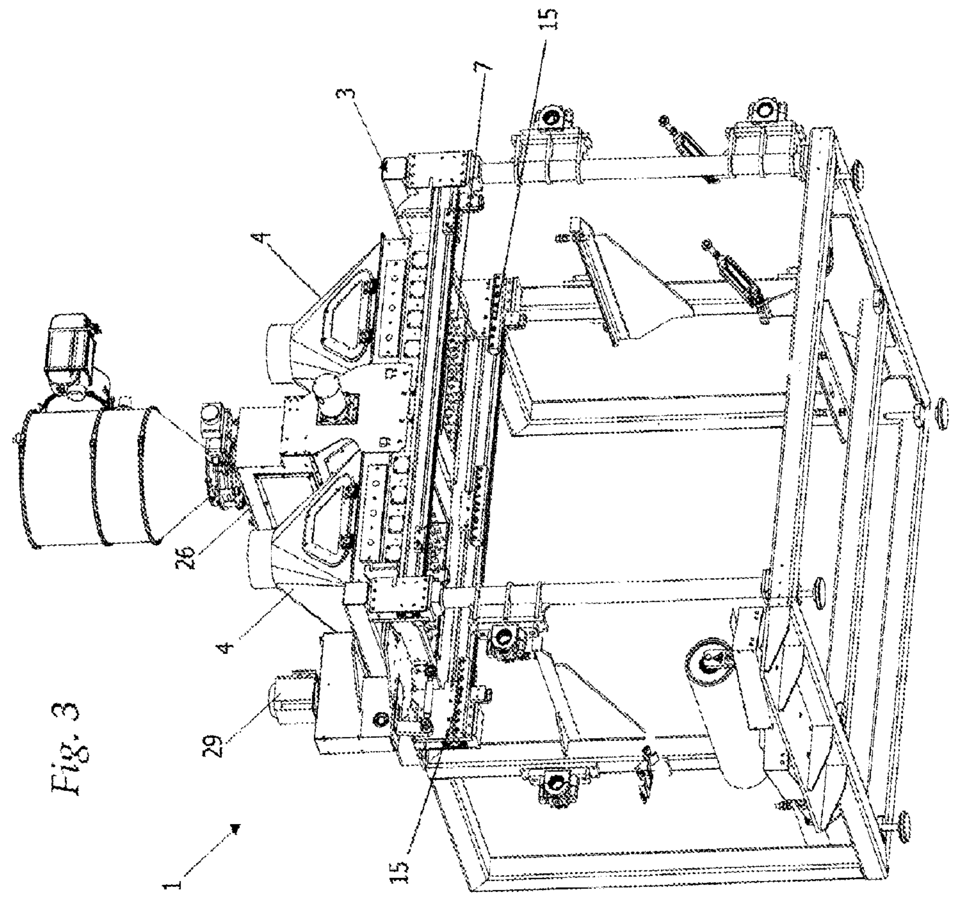
FIG. 3 shows, in axonometric view from below, part of the forming station of FIG. 1.

With particular reference to FIG. 3, said frame 3 is adapted to create a supporting and fixing structure, for example for the two ducts 4 in which the flow of cellulose flakes flows, for the rotating brushes 7, and for the motor means 28, 29.

Said ducts 4 are arranged in sequence in the feed direction x of said ply 2.

Between said ducts 4 for passage of the flow of cellulose flakes, a feed duct 26 is positioned for superabsorbent material which in some cases can be contained in the absorbent core itself.

Said ply 2 is fed in direction x supported by a perforated belt 5 closed in a ring and rotated by a plurality of motorized or relay rollers 33.

Said belt 5 is perforated to allow suction by the hood 6 below.

Figures 4, 5, 6:
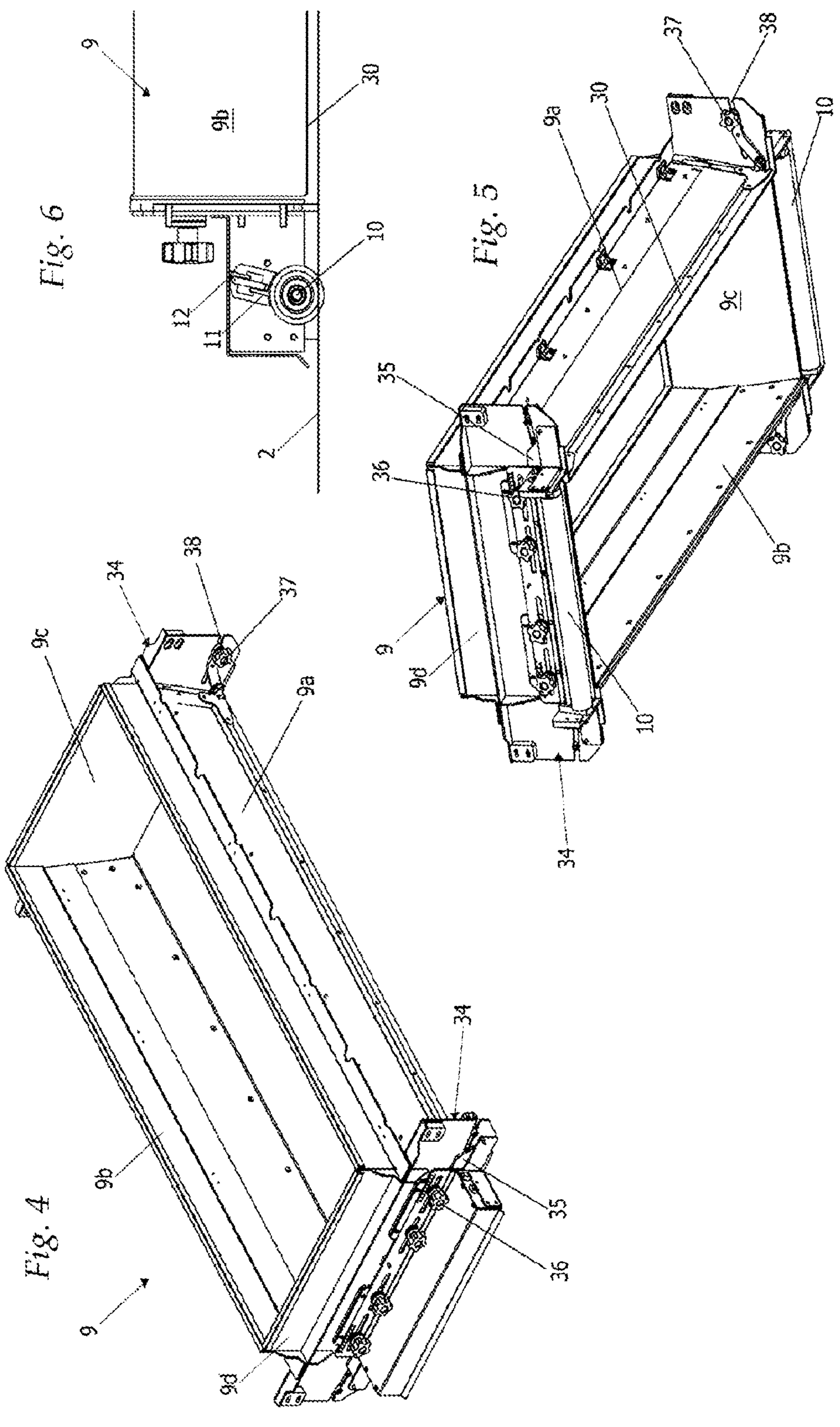
FIGS. 4 and 5 show, in axonometric view from two different angles, details of the forming station according to the invention.
FIG. 6 shows, in section, a detail of FIG. 5.

With particular reference to FIGS. 4-6, said collection unit 9 is illustrated, in which the uniformly distributed cellulose flakes are deposited on said ply 2.

Said collection unit 9 comprises a first pair of lateral walls **9*a*, 9*b* parallel to the feed direction x of said ply 2 and a second pair of lateral walls 9*c*, 9*d* orthogonal to said feed direction x, in addition to an assembly frame 34**.

At least said lateral walls **9*a*, 9*b* parallel to the feed direction x comprise, along their edge facing said ply, a felt profile 30** which creates an airtight surround.

It must be possible for said suction hood 6 to place said collection unit 9 in a vacuum; the latter must therefore have an inner dimension corresponding to the actual dimension of the absorbent core to be produced and it must be airtight.

For said purposes, said forming station 1 comprises adjustment means for adjusting the reciprocal position of said lateral walls **9*a*, 9*b* parallel to the feed direction x of said ply 2, to vary the dimension of said collection unit 9** according to the width of the ply.

Said adjustment means, which act at both ends of said collection unit 9 in the feed direction x of said ply 2, comprise:

- stop plates 35 movable and selectively fixable in a position by means of first handwheels 36, where said position predetermines the dimension, in particular the width, of said collection unit 9;
- second handwheels 37 adapted to guide, along a cam profile 38 obtained on said assembly frame 34, the displacement of said lateral walls **9*a*, 9*b* parallel to the feed direction x of said ply 2 until touching said stop plates 35**, and then fix the reciprocal position thereof.

For the purposes of the peripheral airtightness of said collection unit 9, each lateral wall **9*c*, 9*d* orthogonal to said feed direction x comprises an idle rubber-coated roller 10 adapted to rest, rolling, on said ply 2 (FIG. 5**).

Said idle rubber-coated rollers 10 allow said collection unit 9 to be closed in an airtight manner, at the same time allowing feed of the ply 2 without the risk of tearing.

Said collection unit 9 also comprises a further seal system with scraper blades 11, 12; said blades 11, 12, the position of which is manually adjustable, behave like scrapers and are adapted to slide on said idle rubber-coated rollers 10 and create a seal against the sheet metal that forms the assembly frame 34 of said collection unit 9 (FIG. 6).

Said seal systems are essential to guarantee good suction of the cellulose flakes and prevent air gaps that could create turbulence such as to compromise uniform deposit of the cellulose on the ply 2.

With particular reference to FIG. 7, said screen 8 comprises two portions provided with holes 8' for the passage of the cellulose flakes, arranged substantially below said cellulose feed ducts 4, and a central opening 27 directly connected to said feed duct 26 for feeding superabsorbent material, thus favouring direct deposition thereof on the ply 2, between a first and a second layer of cellulose.

Since said screen 8 moves with an alternating translation movement in the feed direction of the ply 2, said screen 8 comprises wheels 16 and said frame 3 comprises corresponding tracks 15 (FIG. 3) adapted to cooperate with said wheels 16.

With particular reference to the detail section of FIG. 8, said "come and go" alternating movement means of said screen 8 are illustrated.

In particular, said movement means comprise a mechanism with connecting rod 13 and crank 14.

Said connecting rod 13 comprises a first 13' and a second 13" end.

Said crank is produced by means of a wheel 14 on which a first end 13' of said connecting rod 13 is fixed off-centre.

The second end 13" of said connecting rod 13 is connected to said screen 8 by means of a linkage 39 of first type with two arms and a rod 40 with two hinges.

Said linkage 39 is hinged to said frame 3 and comprises a first 39' and a second 39" end.

Said first end 39' of said linkage 39 is connected to the second end 13" of said connecting rod 13.

Said second end 39" of said linkage 39 is connected to a first end 40' of said rod 40 with two hinges.

A second end 40" of said rod 40 with two hinges is then connected to said screen 8.

To adjust the range of the "come and go" alternating movement of said screen 8, to modify the density of the cellulose deposited on the ply 2 and to take account of the final dimensions of the absorbent core, said crank 14 comprises, along a radius thereof, selective fixing means for the first end 13' of said connecting rod 13.

Said selective fixing means comprise an adjustment screw 41 adapted to be moved along the operative radius of the crank 14: a shorter radius results in a reduced range of the alternating movement of the screen 8; vice versa, a longer radius results in a wider range of the alternating movement.

With particular reference to FIG. 9-13, said suction hood 6 is illustrated, positioned below the perforated belt 5 supporting the ply 2.

Said suction hood 6 comprises essentially an extractor 17 with horizontal axis, a horizontal conveyor 18 and a vertical conveyor 19, joined to one another by means of a flange 20.

Said horizontal conveyor 18 comprises a suction inlet 21 over which said perforated belt 5 runs, on which said ply 2 rests.

Said suction inlet 21 comprises blade shuttering means for adjusting the opening thereof.

Said blade shuttering means comprise two plates 22 sliding on the plane that contains said suction inlet 21 transversally to the feed direction x of said ply 2.

The sliding of said plates 22 narrows or widens said suction inlet 21 according to the width of the ply 2 being fed forward.

Said conveyors 18, 19 each comprise a plurality of inner walls 18', 19' that divide them into horizontal chambers 23 and vertical chambers 24.

Advantageously, said suction hood 6 can also vary its suction flow rate, selectively closing the section of said chambers 23, 24.

Said horizontal conveyor 18 and vertical conveyor 19 comprise shutters 25, revolvingly associated with said walls 18', 19' by means of hinges.

Said horizontal conveyor 18 and vertical conveyor 19 comprise control means for said shutters 25 that can be operated from the outside.

Said control means comprise, for each shutter 25:

- a slot 42 obtained on an outer lateral wall of the respective conveyor 18, 19;
- a control pin 43 associated with said shutter 25, passing through said slot 42 so that it protrudes on the outside of said suction hood 6, and sliding inside it;
- locking means for locking a selected position of said control pin 43 in said slot 42.

For each control pin 43, said locking means comprise a pin 44 stably associated on the same outer lateral wall of the conveyor 18, 19 on which said slot 42 is obtained, and a comb 45, associated with said control pin 43, the teeth of which are adapted to cooperate with said pin 44 to maintain the position of the control pin 43 fixed inside the slot 42, and consequently to maintain fixed the inclination of the respective shutter 25 relative to the inner wall 18', 19' of the conveyor 18, 19 to which it is hinged.

The operation of the forming station 1 is as follows.

The ply 2 is fed into the forming station 1 in a feed direction x, forced by the suction hood to rest on said perforated belt 5.

The cellulose flakes, coming from a grinding mill, are blown into said feed ducts 4.

The cellulose flakes are sucked by said suction hood 6 facilitated by the combined rotation movement of the brushes 7.

As the brushes 7 rotate, they lightly touch said screen 8 and accompany the cellulose flakes through the screen holes 8'.

The simultaneous "come and go" alternating movement of the screen 8 ensures uniform distribution of the cellulose on the ply 2 below.

The invention claimed is:

1. A forming station for forming an absorbent core for disposable hygiene products, the absorbent core comprising at least one ply having cellulose flakes deposited thereon, said forming station comprising:

- a frame;
- at least one cellulose feed duct configured to convey a flow of cellulose flakes;
- a ply feeding assembly configured to advance the ply in a feed direction;
- a perforated belt configured to support said ply as the ply advances in the feed direction;
- a suction hood, positioned below said perforated belt, and configured to draw said cellulose flakes toward said ply;
- a plurality of rotating brushes, each rotating brush having a horizontal axis of rotation and being oriented transverse to the feed direction of said ply;
- a screen positioned between said plurality of rotating brushes and said ply, the screen comprising a plurality of holes extending therethrough;
- a reciprocating drive mechanism operatively connected to the screen and configured to reciprocate said screen in an alternating motion parallel to the feed direction of said ply;
- wherein said plurality of rotating brushes are positioned to contact said screen during rotation, and
- wherein said cellulose flakes pass through said plurality of holes in said screen and are deposited on the ply by the combined action of: suction from said suction hood, rotation of said plurality of rotating brushes, and reciprocating motion of said screen.

2. The forming station according to claim 1, further comprising a collection chamber disposed between said screen and said perforated belt, the collection chamber having a peripherally sealed enclosure configured to be placed under a vacuum by said suction hood.

3. The forming station according to claim 2, wherein said collection chamber comprises a first pair of lateral walls oriented parallel to the feed direction of said ply, and a second pair of lateral walls oriented orthogonal to the feed direction of the ply.

4. The forming station according to claim 3, further comprising an adjustment mechanism configured to adjust a position of said first pair of lateral walls relative to each other, thereby varying a width of said collection chamber to accommodate different ply widths.

5. The forming station according to claim 3, wherein each lateral wall of the second pair of lateral walls comprises a roller configured to rest on said ply to seal said collection chamber while permitting the ply to advance in the feed direction.

6. The forming station according to claim 5, wherein said collection chamber further comprises a sealing system comprising scraper blades positioned adjacent to each roller to maintain an airtight seal of the collection chamber.

7. The forming station according to claim 1, wherein the reciprocating drive mechanism comprises a connecting rod and crank mechanism operatively connected to the screen.

8. The forming station according to claim 7, wherein said crank comprises a wheel having, a spoke, and said connecting rod, is selectively attachable to the spoke at different radial positions to adjust a stroke length of the reciprocating motion of the screen.

9. The forming station according to claim 1, wherein said frame comprises one or more tracks, and said screen comprises one or more wheels configured to travel along the one or more tracks during the reciprocating motion.

10. The forming station according to claim 1, wherein said suction hood comprises an extractor, a horizontal conveyor section, and a vertical conveyor section, wherein the extractor, horizontal conveyor section, and vertical conveyor section are joined to one another by a flange.

11. The forming station according to claim 10, wherein said horizontal conveyor section comprises a suction inlet over which said perforated belt travels, with said ply resting thereon, and said suction inlet comprises adjustable blade shutters for adjusting an opening size of the suction inlet.

12. The forming station according to claim 10, wherein said horizontal conveyor section comprises a plurality of inner walls dividing the horizontal conveyor section into a plurality of horizontal chambers, and the vertical conveyor section comprises a plurality of inner walls dividing the vertical conveyor section into a plurality of vertical chambers.

13. The forming station according to claim 12, further comprising a plurality of shutters configured to regulate suction flow through the plurality of horizontal chambers and the plurality of vertical chambers.

14. The forming station according to claim 13, wherein each shutter of the plurality of shutters comprises an externally accessible control mechanism configured to adjust a position of the shutter from outside the suction hood.

15. The forming station according to claim 1, further comprising a second cellulose feed duct, wherein the at least one cellulose feed duct and the second cellulose feed duct are arranged in series along the feed direction of said ply; and a super-absorbent material feed duct positioned between the at least one cellulose feed duct and the second cellulose feed duct.

16. The forming station according to claim 15, wherein said screen comprises a central opening aligned with the super-absorbent material feed duct to permit deposition of super-absorbent material onto the ply between a first layer of cellulose flakes and a second layer of cellulose flakes.

17. A method of forming an absorbent core for disposable hygiene products, the method comprising:

advancing a ply in a feed direction on a perforated belt;

conveying cellulose flakes through at least one feed duct toward the ply;

passing the cellulose flakes through a perforated screen positioned between the at least one feed duct and the ply, the perforated screen having a plurality of holes;

rotating a plurality of brushes in contact with the perforated screen to urge the cellulose flakes through the plurality of holes;

reciprocating the perforated screen in an alternating motion parallel to the feed direction while the plurality of brushes rotate; and drawing the cellulose flakes through the perforated screen and onto the ply using suction applied from below the perforated belt, whereby the cellulose flakes are uniformly distributed on the ply by the combined action of brush rotation, screen reciprocation, and suction.

18. A forming station for forming an absorbent core, comprising:

a support structure;

a material distribution system comprising:

a feed duct for conveying particulate material;

a reciprocating perforated screen positioned to receive the particulate material from the feed duct;

a plurality of rotating brushes in contact with the reciprocating perforated screen; and a suction device positioned to draw the particulate material through holes in the reciprocating perforated screen;

a substrate transport mechanism configured to advance a substrate beneath the reciprocating perforated screen in a feed direction; and a reciprocating drive mechanism configured to move the reciprocating perforated screen in an alternating linear motion parallel to the feed direction while the plurality of rotating brushes rotate, whereby the particulate material is uniformly distributed on the substrate.

* * * * *